US00RE42837E

(19) United States
(12) Reissued Patent
Stoy et al.

(10) Patent Number: US RE42,837 E
(45) Date of Reissued Patent: Oct. 11, 2011

(54) SPINAL NUCLEUS IMPLANT

(75) Inventors: Vladimir Stoy, Praha Zapad (CZ); Gerald Gontarz, Jr., Spotswood, NJ (US)

(73) Assignee: Replication Medical, Inc., Cranbury, NJ (US)

(21) Appl. No.: 10/625,390

(22) Filed: Jul. 23, 2003

Related U.S. Patent Documents

Reissue of:
(64) Patent No.: 6,264,695
Issued: Jul. 24, 2001
Appl. No.: 09/410,268
PCT Filed: Sep. 30, 1999

(51) Int. Cl.
*A61F 2/44* (2006.01)
(52) U.S. Cl. ..... 623/17.16
(58) Field of Classification Search ..... 623/17.11–17.16
See application file for complete search history.

(56) References Cited

U.S. PATENT DOCUMENTS

| | | | | | |
|---|---|---|---|---|---|
| 3,875,595 | A | * | 4/1975 | Froning | 623/17.12 |
| 4,107,121 | A | * | 8/1978 | Stoy | 524/391 |
| 4,220,152 | A | * | 9/1980 | Dresback | 424/439 |
| 4,309,777 | A | * | 1/1982 | Patil | 623/17.13 |
| 4,331,783 | A | * | 5/1982 | Stoy | 525/294 |
| 4,337,327 | A | * | 6/1982 | Stoy | 525/280 |
| 4,349,921 | A | * | 9/1982 | Kuntz | 623/17.16 |
| 4,369,294 | A | * | 1/1983 | Stoy | 525/340 |
| 4,370,451 | A | * | 1/1983 | Stoy | 525/294 |
| 4,379,874 | A | * | 4/1983 | Stoy | 524/27 |
| 4,420,589 | A | * | 12/1983 | Stoy | 525/93 |
| 4,636,217 | A | * | 1/1987 | Ogilvie et al. | 623/17.11 |
| 4,714,469 | A | * | 12/1987 | Kenna | 606/86 A |
| 4,759,769 | A | * | 7/1988 | Hedman et al. | 623/17.13 |
| 4,772,287 | A | * | 9/1988 | Ray et al. | 623/17.12 |
| 4,837,111 | A | * | 6/1989 | Deters et al. | 424/473 |
| 4,863,476 | A | * | 9/1989 | Shepperd | 623/17.15 |
| 4,867,969 | A | * | 9/1989 | Magruder et al. | 424/679 |
| 4,904,260 | A | * | 2/1990 | Ray et al. | 623/17.12 |
| 4,904,261 | A | * | 2/1990 | Dove et al. | 623/17.16 |

(Continued)

FOREIGN PATENT DOCUMENTS

EP 0 505 634 A1 9/1992

(Continued)

OTHER PUBLICATIONS

Hudgins, Robert Garryl, Development and Characterization of a Prosthetic Intervertebral Disc, Published Aug. 16, 1999 (on information and belief); Copyright 1998, ISBN 978-0-599-17460-3.

(Continued)

*Primary Examiner* — Alvin J Stewart
(74) *Attorney, Agent, or Firm* — Carter, DeLuca, Farrell & Schmidt, LLP

(57) ABSTRACT

The present invention is a spinal nucleus implant for replacement of at least a portion of nucleus pulposus tissue removed from a spinal disc of a living vertebrate to restore function of the spinal disc and related vertebral joint. The implant is an anisotropically swellable, biomimetic xerogel plastic, having a two phase structure with a hydrophobic phase having high crystallinity and low water content and with hydrophilic phase having low crystallinity and high water content and having a negatively charged lubricious surface. The xerogel plastic is capable of rehydration and of osmotic movement of liquid therethrough in response to osmotic pressure change to thereby increase and decrease liquid content in its hydrated state. The present invention also relates to surgical implant procedures utilizing this spinal nucleus implant.

50 Claims, 3 Drawing Sheets

U.S. PATENT DOCUMENTS

| | | | | | |
|---|---|---|---|---|---|
| 4,911,718 | A | * | 3/1990 | Lee et al. | 623/17.15 |
| 4,943,618 | A | * | 7/1990 | Stoy et al. | 525/340 |
| 5,047,055 | A | * | 9/1991 | Bao et al. | 623/17.16 |
| 5,053,034 | A | * | 10/1991 | Olerud | 606/246 |
| 5,171,280 | A | * | 12/1992 | Baumgartner | 623/17.12 |
| 5,192,326 | A | * | 3/1993 | Bao et al. | 623/17.12 |
| 5,252,692 | A | * | 10/1993 | Lovy et al. | 526/342 |
| 5,489,308 | A | * | 2/1996 | Kuslich et al. | 623/17.11 |
| 5,534,028 | A | * | 7/1996 | Bao et al. | 623/17.16 |
| 5,674,295 | A | * | 10/1997 | Ray et al. | 623/17.12 |
| 5,674,296 | A | * | 10/1997 | Bryan et al. | 623/17.16 |
| 5,676,701 | A | * | 10/1997 | Yuan et al. | 623/17.15 |
| 5,716,415 | A | * | 2/1998 | Steffee | 623/17.16 |
| 5,824,093 | A | * | 10/1998 | Ray et al. | 623/17.16 |
| 5,824,094 | A | * | 10/1998 | Serhan et al. | 623/17.16 |
| 5,863,551 | A | * | 1/1999 | Woerly | 424/423 |
| 5,865,846 | A | * | 2/1999 | Bryan et al. | 128/898 |
| 5,879,385 | A | * | 3/1999 | Crockard et al. | 623/17.11 |
| 5,976,186 | A | * | 11/1999 | Bao et al. | 623/17.16 |
| 6,110,210 | A | * | 8/2000 | Norton et al. | 623/17.16 |
| 6,165,225 | A | * | 12/2000 | Antanavich et al. | 623/23.72 |
| 6,264,695 | B1 | * | 7/2001 | Stoy | 623/17.16 |
| 6,764,514 | B1 | * | 7/2004 | Li et al. | 623/17.12 |
| 7,004,971 | B2 | * | 2/2006 | Serhan et al. | 623/17.16 |
| 7,204,897 | B2 | * | 4/2007 | Stoy et al. | 156/61 |
| 7,368,862 | B2 | * | 5/2008 | Pelrine et al. | 310/365 |
| 2002/0183848 | A1 | * | 12/2002 | Ray et al. | 623/17.12 |
| 2003/0023311 | A1 | * | 1/2003 | Trieu | 623/17.16 |

FOREIGN PATENT DOCUMENTS

| | | |
|---|---|---|
| WO | WO 00/64385 | 11/2000 |
| WO | WO 02/076336 A2 | 10/2002 |

OTHER PUBLICATIONS

Hudgins, R. Garryl, and Muzzy, John D., Polymer Composites, vol. 19, No. 6, 1998, pp. 837-845.

* cited by examiner

SPINAL NUCLEUS IMPLANT

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to a spinal nucleus implant to replace all or a portion of nucleus pulposus which has been removed form a spinal disc of a living vertebrate, e.g. a human. This spinal nucleus implant is formed of a xerogel which is capable of anisotropic swelling.

2. Information Disclosure Statement

Spinal intervertebral disc is a cartilaginous tissue located between the endplates of adjacent vertebra. The spinal intervertebral disc acts as a flexible joint between the vertebra, allowing bending and twisting of the spine column. Damage to the spinal intervertebral disc can cause spinal dysfunction, crippling pain and short- or long-term disability. Because of the wide occurrence of this problem (5% annual incidence of back pain due to the spinal intervertebral disc is reported), the economic consequences are enormous. Some disc problems require a surgery. Typical current procedure is fusion of the adjacent vertebra using various techniques and devices, such as those described in the U.S. Pat. No., 4,636,217 (Ogilvie, et al.), U.S. Pat. No. 5,489,308 (Kuslich, et al.) and U.S. Pat. No. 5,716,415 (Steffee). All currently available surgical procedures, such as removal of the nucleus or its part (laminectomy), or fusion of adjacent vertebra, compronise spinal function in one way or another.

For this reason, new remedies are being sought, including the development of prosthesis of the disc or its part. This is a difficult undertaking. The spinal column is an extremely intricate body part, and its proper function is dependent on the seamless cooperation of all its components, including the vertebral discs. A vertebral disc has to perform multiple functions. It has to withstand repeated high stresses in very complex modes of deformation including combined bending, torque, shear and compression. In addition, the spinal intervertebral disc acts as an efficient shock absorber and a pump driving a flow of nutrients into and metabolites from the disc. Structurally, the disc is a rather complex composite part involving several types of materials organized in a complex and intricate fashion. Vertebral endplates are covered by a layer of hyaline cartilage composed of a collagen matrix, a glycoprotein component, and water. In addition, about 2-5% of its volume is occupied by living cells producing the components of the cartilage.

The spinal intervertebral disc itself is composed mainly of crystalline collagen fibrils and amorphous hydrophilic proteoglycans. About 3-5% of the volume is occupied by living cells that produce the its constituents. Structurally, the spinal intervertebral disc is composed of a hydrogel-like core called the nucleus pulposus; and an outside ring called the annulus fibrosus. The structure of the spinal intervertebral disc is schematically depicted in FIG. 1 and described below.

The spinal intervertebral disc acts primarily as a weight-bearing and flexible joint. It enables mutual rotation, bending and translation of the adjacent vertebra, while bearing a considerable axial load. In addition, the spinal intervertebral disc attenuates vibrations and mechanical shocks and prevents their propagation through the skeletal system The load bearing capability and flexibility in selected directions is achieved by the combination of the annulus fibrosus and nucleus pulposus. Annulus fibrosus is a layered structure that is rigid in the radial direction but deformable in the axial direction and by torque. The axial load is born by nucleus pulposus that transforms it partly into an axial component that is contained by the annulus fibrosus. The annulus fibrosus is formed mainly by collagen fibrils organized in several layers. Each layer has its collagen fibrils wound at an angle, and subsequent layers have an alternate orientation. The collagen organization closely resembles organization of fiber reinforcement as in composites used for pressure vessels or cords in tires. It guarantees maximum resistance to radial stress (or internal pressure) while allowing a deformation in torque and bending.

The fibril ends are attached to the adjacent vertebra and to the cartilaginous surface of the vertebral endplates. Consequently, the inner space of the annulus fibrosus is virtually sealed. Any liquid penetrating in or out of the core has to pass through the annulus fibrosus tissue or through the vertebral endplates. To achieve sufficient hydraulic permeability, the collagenous structure of the annulus fibrosus is supplemented by proteoglycans embedded between the collagen fibrils. The proteoglycans are hydrated so that the annulus fibrosus forms a sort of a highly organized, anisotropic hydrogel composite. The collagen domains form a microfibrillar mesh. The result of this arrangement is a sufficient deformability in selected directions combined with high mechanical strength, and particularly high tear strength and resistance to fracture propagation that are needed for a load-bearing function.

The nucleus pulposus is connected to the annulus fibrosus, but not to the endplates. It has much a lower concentration of collagen (which concentration increases with age) and a higher concentration of hydrophilic proteoglycans. Consequently, it is a natural composite which is somewhat like a hydrogel and has a very high equilibrium water content (more than 90% by weight in young persons). The water content and volume of nucleus pulposus depends on osmolarity of swelling medium and on the mechanical pressure. The resistance to the decrease of liquid content due to mechanical pressure is called the "swelling pressure". Swelling pressure is the very key to the function of the nucleus pulposus. As the axial load expels the liquid, the swelling pressure increases until it reaches equilibrium with the external load. Accordingly, the nucleus pulposus is capable of counterbalancing and redistributing the axial stress, converting them to radial components that can be confined by the annulus fibrosus. In addition, the dehydration and rehydration of nucleus pulposus under varying load drives the transport of metabolites and nutrients in and out the spinal intervertebral disc. Therefore, the nucleus pulposus acts as an osmotic pump facilitating transport of nutrient and metabolites to and from the spinal disc and surrounding tissues. This transport function is essential because the cartilaginous components (annulus fibrosus, nucleus pulposus and cartilaginous layer of the vertebral endplates) are neither vascularized nor can be supported with nutrition by mere diffusion.

Since the nucleus pulposus is substantially a macroscopically isotropic tissue, it has to be organized on its molecular and supermolecular levels to perform all these functions.

The nucleus pulposus structure is rather ingenious. The nucleus pulposus is constructed from a two-phase composite consisting of crystalline collagen domains forming a scaffold, and amorphous glycoprotein domains forming hydrophilic filler. The crystalline collagen domains are responsible for a relatively high strength even at high hydration. They form a microfibrillar mesh resembling the fibrous reinforcement in high-performance composites. The result of this arrangement is a sufficient deformability combined with sufficient mechanical strength even at full hydration.

The amorphous domains are responsible for water absorption and for the generation of a swelling pressure. They are formed mainly by high-molecular, water-soluble glycoproteoglycans. Glycoproteoglycans are highly hydrophilic and water-soluble polymers. A small portion of glycoaminoglycans is covalently bound to the coilagenous scaffold, turning it hydrophilic and highly wettable with water (this is necessary for the thermodynamic stability of the two-phase composite). A large portion is unattached to the scaffold and is retained by an entrapment within the scaffold due to the large size of glycoproteoglycans molecules.

To help this physical retention, glycoproteoglycans chains associate to form larger units. Glycoproteoglycans chains are equipped with protein terminal sequences adjusted for attachment to hyaluronic acid. The complexes of the hyaluronic acid and GPG are too large to escape from the collagenous scaffold. This is a very different arrangement than in hydrogels where the confinement of hydrophilic moieties is achieved by crossliking. One can surmise that the arrangement in the nucleus pulposus provides a higher osmotic pressure at a given polymer concentration than the network arrangement usual in hydrogels.

The glycoproteoglycans in the amorphous phase bear a dense negative charge. The high negative charge density is important because it generates high values of viral coefficients and, therefore, causes maximum swelling pressure at a high water content. The high charge density is facilitated by the composite structure of the nucleus pulposus. A synthetic crosslinked hydrogel with a similar charge density would be brittle and mechanically very weak.

A high negative charge is also responsible for a high surface hydration that is necessary for a low wet friction. This is important for the low-friction contact between the nucleus pulposus and the cartilaginous surfaces of vertebral end plates. A high friction would probably cause an excessive wear of the cartilage and degenerative changes in vertebra.

This structural complexity of spinal intervertebral disc is the consequence of complex requirements, not a whimsical excess of nature. Therefore, the disc replacement's function, properties and structure has to be a close approximation of the original disc in order to be able to perform all its functions. In other words, a successful disc replacement has to be biomimetic to the maximum degree achievable.

This was not possible for a long time because there were no synthetic materials that could replicate structure, properties and functions of natural tissue. Because of that, most of the prostheses were designed as mechanical joints enabling certain movement of vertebra but not replicating all SID properties. Such prostheses are described, for instance, in the following U.S. patents:

U.S. Pat. No. 3,875,595 (Froning); U.S. Pat. No. 4,349,921 (Kuntz); U.S. Pat. No. 4,309,777 (Patil); U.S. Pat. No. 4,714,469 (Kenna); U.S. Pat. No. 4,904,261 (Dove, et al.); U.S. Pat. No. 4,759,769 (Hedman, et al.); U.S. Pat. No. 4,863,476 (Shepperd); U.S. Pat. No. 5,053,034 (Olerud); U.S. Pat. No. 5,674,296 (Bryan, et al.); U.S. Pat. No. 5,676,701 (Yuan, et aL); U.S. Pat. No. 5,824,094 (Serhan, et al.); U.S. Pat. No. 5,865,846 (Bryan, et al).

The main problem of these devices is limited functionality. Even more importantly, implantation of these devices is a very complex procedure requiring a major spine surgery with many associated risks, long-term recovery and high cost.

There is an ongoing effort to develop better prosthesis of the disc that would more closely replicate its mechanical function. For instance, Lee et aL in the U.S. Pat. No. 4,911,718 "Functional and Biocompatible Intervertebral Spacer" (1990) describe a composite replacement of the disc made from a biocompatible elastomer reinforced with fibers that mimics the mechanical properties of the natural disc. It replicates the disc structure having an elastomeric core with the shape approximating the shape of nucleus pulposus, wrapped around by a fiber-reinforced elastomeric layers replicating structure of annulus fibrosus. The reinforcing fibers have preferred orientation-simulating arrangement of collagen fibers in annulus fibrosus. The faces of the assembly are equipped with tough elastomeric layers simulating the mechanical function of cartilaginous layers of vertebral endplates. This structure reasonably closely replicates the spinal intervertebral disc structure and its mechanical function. However, the implantation of this device is still very complex and costly, requiring a major spine surgery.

In many cases, the pain relief requires that only nucleus pulposus (or even only its part) be removed rather than whole spinal intervertebral disc. In that case, the major part of the axial load is directly applied to annulus fibrosus. Annulus fibrosus is now stressed by the axial rather than radial load for which it is designed. Consequently, annulus fibrosus delaminates, splits, fractures and brakes down gradually. The situation is somewhat akin to driving on a deflated tire. In this situation, it is useful to replace the missing nucleus pulposus (or its part) to reestablish the radial stress on annulus fibrosus (or to "reinflate" the spinal intervertebral disc) that is required for its proper function. The nucleus pulposus replacement can be carried out by an easier, less traumatic and less expensive surgical procedure.

It is important to recognize that a successful replacement of nucleus pulposus has to replicate not only the mechanical function, but also the function of osmotic pump. Without that, the living tissue of vertebral endplate cartilages and annulus fibrosus cannot be maintained in healthy condition. For those reasons, the nucleus pulposus cannot be replaced by a piece of a hydrophobic, non-hydrogel elastomer, such as silicone rubber or polyurethane.

This need to maintain the liquid transport function was first recognized by Bao et al. in the U.S. Pat. No. 5,047,055. Bao describes a hydrogel prosthesis that has, in its fully hydrated state, the shape and size generally conforming to a missing natural nucleus, i.e., to the cavity left after removal of nucleus pulposus tissue. The hydrogel used in the implant has, in its fully hydrated state, water content at least 30% and compressive strength at least 4 $MN/m^2$ (i.e., 40 $kg/cm^2$ or 556 psi). This high strength has to be achieved even at full hydration and at a very high water content, such as in the preferred range 70 to 90% of liquid. Conceivably, this very high requirement on mechanical strength is dictated by possible herniation of isotropic material that was implanted into damaged and weakened annulus fibrosus. This rather extreme requirement limits selection of materials useful for this device, Hydrogels are typically weaker than other plastics and rubbers, particularly at high water content. Therefore, selection of high-swelling hydrogels with such a high compressive strength is rather narrow.

The hydrogel prostheses according to Bao is implanted in partly or fully dehydrated shape when it is undersized, i.e. its volume is 10-70% of the volume of fully hydrated hydrogel implant. Consequently, the hydrogel implant can be inserted through a small incision and then grow into its full size by absorbing aqueous body fluids. The hydrogel used for the implant has in its fully hydrated state water content higher than 30%, and preferably between 70 and 90% of liquid. The materials used by Bao are isotropic so that the implant's expansion due to hydration is equal in all directions. The implant can be composed from 2 or more pieces of combined size and shape, if fully hydrated, of the cavity vacated by the nucleus pulposus removal.

There are several shortcomings of this concept. Hydrogel expansion is limited to the size of the cavity vacated by the nucleus pulposus, so that its swelling pressure at the fully hydrated and expanded state will be very low, or even zero. Therefore, the implant will not generate sufficient axial force for the vertebral separation that can be found in the healthy spinal intervertebral disc. This is different from natural nucleus pulposus that is underswelled inside the spinal intervertebral disc and generates positive swelling pressure even at maximum vertebral separation. Bao could not use such an "oversized design" because the spinal nucleus implant is implanted into a damaged annulus fibrosus (either due to surgical incision or due to the original injury) and expansion of the spinal nucleus implant beyond the cavity size would cause its extrusion similar to herniation of natural nucleus pulposus. As Bao notes, bulging of the implant under stress is prevented by resistance of annulus fibrosus to deformation. Because the integrity of annulus fibrosus is compromised, hydrogel used in prosthesis has to be much stronger than natural nucleus pulposus to resist herniation or extrusion (namely, more than 4 MN/sq.m at full hydration).

This limitation is caused by the fact that the swelling of the Bao's the spinal nucleus implant is isotropic, namely, it is the same in radial and axial directions. Consequently, extensive expansion in axial direction would cause comparable expansion in radial direction that would generate pressure against the damaged annulus fibrosus and cause it rupture, bulging or herniation. In addition, the hydrogels of the kind described by Bao are isotropic elastomers, with the same deformability in any direction. In the described design, the axial load will cause radial deformation, that will be the largest in the direction of the least resistance, i.e. in locations where annulus fibrosus has been weakened by the surgery or by previous injury to the disc. This may result in bulging, herniation or extrusion of the implant—problems similar to the disc damage that was the reason for the surgery in the first place.

Some of these shortcomings were addressed in subsequent invention by Bao et al. described in the U.S. Pat. No. 5,192,326. The prosthetic nucleus is formed by a multiplicity of hydrogel beads having water content at least 30%, said beads being surrounded by a flexible semipermeable cover. The porous cover has, if fully extended, the size and shape of the cavity vacated by the nucleus pulposus removal. The size of the beads is at least three times larger than size of the pores in said cover so that the hydrogel is safely confined within the cover. The hydrogel beads can contain as much as 99% of liquid if fully hydrated. The overall volume of the fully hydrated hydrogel beads may be greater that the volume of the cavity vacated by the nucleus pulposus removal, because casing restricts the swelling and prevents the hydrogel expansion beyond the internal volume and dimensions of the cover. The cover can be made of knitted fibers. Preferably, the casing is coated by a highly biocompatible polymer to prevent adverse reactions to the implant. However, even with a coating the microporous casing may induce a foreign body reaction, initiate protein deposition, become loci of bacterial colonization or cause other problems. The use of the cover sacrifices some advantages of hydrogels, such as high biocompatibility and surface lubricity. In addition, the beads have relatively low packing density and relatively large interstitial space fraction.

Ray et al. invented somewhat similar designs to '326. In the U.S. Pat. No. 4,772,287 Ray describes a implant into the nucleus pulposus composed of two flexible cylindrical bladders filled with a liquid, preferably a thixotropic liquid. The bladders are surrounded by strong fibrous casing, preferably combined with a biodegradable polymer that promotes tissue in growth. Optionally, the bladders are equipped by tubing for adding or withdrawing fluid. This device obviously does not replicate the shape and properties of nucleus pulposus, only attempts to simulate some of its functions. The fibrous casing is designed to facilitate integration of the implant into the residual spinal intervertebral disc tissue, causing thus partial fusion of the vertebral joint.

In the U.S. Pat. No. 4,904,260 Ray describes an improvement of his basic design in which the capsule is made of a semipermeable material and filled with an aqueous liquid containing a therapeutic material capable of a slow diffusion from the implant into the tissue.

In the U.S. Pat. No. 5,674,295 Ray describes another improvement of his basic design in which a hydrogel cylindrical body is used instead of the liquid-filled bladder. The strong fibrous casing is designed to allow more swelling in axial direction than in radial direction, allowing thus sufficient axial expansion while protecting annulus fibrosus against excessive pressure from the expanding and/or deformed hydrogel This design is further modified in the U.S. Pat. No. 5,824,093 (continuation-in-part to the '295) where the hydrogel bodies have oval crossections and the constraining jacket designed to maintain the general shape of the hydrogel under full hydration and load.

In all Ray's designs the device is not mimicking the nucleus pulposus shape, size, properties or full function. The volume of the hydrated hydrogel is substantially smaller that the natural nucleus pulposus volume. The shape of Ray's implant differs substantially from the nucleus pulposus shape and one could anticipate certain problems with position stability of such implants. To improve the stability, porous or fibrous constraining jacket is incorporated into the residual spinal intervertebral disc tissue. However, this causes a partial fusion, and thus a partial immobilization, of the vertebral joint. The Ray's device does not fill the space designed for nucleus pulposus, which may cause a tendency to distort and to extrude the device under some conditions.

As seen from the description, no prior art invention provides a satisfactory solution to the problem of nucleus pulposus replacement, and neither teaches the present invention nor renders the present invention obvious.

Notwithstanding the prior art, the present invention is neither taught nor rendered obvious thereby.

SUMMARY OF THE INVENTION

This invention relates to a biomimetic spinal nucleus implant designed to restore the function of spinal disc and vertebral joint after a part or all of the nucleus pulposus tissue was removed from the disc of a living vertebrate, e.g. a human. The spinal nucleus implant according to this invention is a swellable plastic device capable of anisotropic swelling into a form of hydrogel implant with anisotropic deformability. The spinal nucleus implant according to the invention is implantable into spinal disc through a small incision facilitating thus the surgery, minimizing the trauma of the surgery and improving the safety of the device.

The invention also relates to the surgical implant procedure relating thereto.

BRIEF DESCRIPTION OF THE DRAWINGS

The present invention should be more fully understood when the specification herein is taken in conjunction with the drawings appended hereto wherein.

DETAILED DESCRIPTION OF THE PRESENT INVENTION

Figure 1:
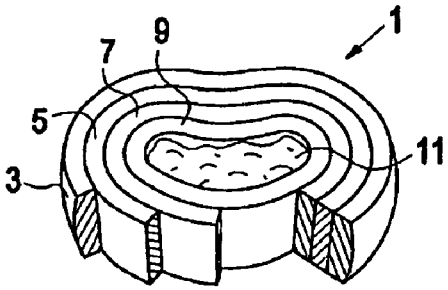
FIG. 1 shows an oblique front view of a cross section of a spinal intervertebral disc and FIG. 2 shows a front expanded cut section of annular fibers of an annulus laminate of a spinal intervertebral disc.

The device according to this invention is designed to replicate the structure and material properties of natural nucleus pulposus to the extent needed to replicate all its essential functions, to achieve position stability of spinal nucleus implant implanted in a weakened annulus fibrosus, and to make spinal nucleus implant implantable through a small incision.

The preferred spinal nucleus implant according to the present invention has properties closely mimicking the essential properties of natural nucleus pulposus, such as:

- Hydrophilic material with equilibrium water content around 90% or higher at full hydration;
- Two-phase structure comprising domains with high crystallinity and lower water content {"hydrophobic domains") and domains with low crystallinity and high water content ("hydrophilic domains").
- High content of carboxylate groups, particularly in hydrophilic domains with high water content and on the surface of the device.
- Associative water-soluble polymers concentrated in hydrophilic domains with higher water content.
- Water content strongly dependent on osmolarity of swelling medium.
- Highly hydrated negatively charged lubricious surface.

The spinal nucleus implant according to the present invention also has the following differences from natural nucleus pulposus:

- The implant size, in its fully hydrated state, does not conform to the natural nucleus pulposus;
- The implant shape, in its fully hydrated state, does not conform to the natural nucleus pulposus;
- Dehydrated implant has anisotropical swelling with preferred swelling in axial direction of spine (vertical plane), and suppressed in the radial direction (horizontal planes);
- The implant has anisotropical deformability (it is more deformable axially and more rigid radially).

These features are explained in more detail below.

In order to replicate or replace the nucleus pulposus functions, the present invention spinal nucleus implant comprises a material capable of swelling in the presence of water and is capable of changing water content in response to external conditions, such as pressure, temperature, osmolarity or pH. They are two types of swellable materials suitable for this invention: More organized hydrophilic composites having some hydrophobicity resembling structure of cartilaginous tissues, and more homogeneous hydrogels.

The present invention hydrophilic composites can be of "cellular" (or "domain") type with continuous hydrophobic domains and discrete hydrophilic domains, and interpenetrating networks where both types of domains are continuous.

The preferred material for the spinal nucleus implant is a synthetic composite of the cellular type with the structure similar to the nucleus pulposus. The structure comprises strong fibrillar crystalline phase, and an amorphous phase comprising charged associative polymers. Polymers involved in the composite are non-biodegradable, preferably with carbon-carbon backbone. The preferred types of polymers are multiblock acrylic polymers. Composites may be of "domain type", in which associative polymers are located in discrete hydrophilic domains; or of a "interpenetrating network" type.

The requirements for the spinal nucleus implant according to the present invention can be also met by certain type of hydrogels. Contrary to composites, hydrogels are formed by a single type of network (covalent, physical or combined). Only hydrogels having certain combination of properties are suitable for the present invention, as described in more detail below.

According to the present invention, height (ie., the axial dimension) of the fully hydrated the spinal nucleus implant is greater than maximum separation between the vertebra in prone position. The fully hydrated diameter of the spinal nucleus implant, however, is substantially the same as the diameter of the cavity vacated by the nucleus pulposus removal.

In the following description, the term "swellable plastic" is used to include both composites and hydrogels.

Swellable plastics contain one or more polymeric components. Preferably, swellable plastics suitable for the spinal nucleus implant comprise polymeric components having C—C backbone. Such polymers, such as polyvinylalcohol, polyvinyl pyrrolidone or derivatives of polyacrylic or polymethacrylic acid, are more resistant to biodegradation than polymers with heteroatoms in their backbones, such as polyurethanes or polyesters.

Preferably, at least on of the polymeric components contains both hydrophilic hydrophobic groups.

The preferred swellable plastic comprises two polymer phases of different hydrophilicity, the less hydrophilic phase having higher content of hydrophobic groups and more hydrophilic phase having higher content of hydrophilic groups. The less hydrophilic phase is preferably crystalline and more hydrophilic phase is preferably amorphous, as can be established from X-ray diffraction.

The preferred hydrophobic groups are pendant nitrile substituents in 1,3 positions on polymethylene backbone, such as in poly(acrylonitrile) or poly(methacrylonitrile). The hydrophilic phase preferably contains a high concentration of ionic groups. Preferred hydrophilic groups are derivatives of acrylic acid and/or methacrylic acids including salts, acrylamidine, N-substituted acrylamidine, acrylamide and N-substituted acryl amide, as well as various combinations thereof. The particularly preferred combination contains approximately two thirds of acrylic acid and its salts (on molar basis), the rest being a combination of plain and N-substituted acrylamides and acrylamidines.

At least one polymeric component is preferably a multiblock copolymer with alternating sequences of hydrophilic and hydrophobic groups. Such sequences are usually capable of separating into two polymer phases and form strong physically crosslinked hydrogels. Such multiblock copolymers can be, for instance, products of hydrolysis or aminolysis of polyacrylonitrile or polymethacrylonitrile and copolymers thereof For the sake of brevity, we will call "PAN" all polymers and copolymers having at least 80 molar % of acrylonitrile and/or methacrylonitrile units in their composition.

Hydrolysis and aminolysis of PAN and products thereof are described, for instance, in the U.S. Pat. Nos. 4,107,121; 4,331,783; 4,337,327; 4,369,294; 4,370,451; 4,379,874; 4,420,589; 4,943,618, and 5,252,692 that are incorporated by this reference.

The swellable plastic can comprise of at least two polymeric components arranged as interpenetrating network. In that case, one component is essentially a hydrophobic polymer capable of forming a reticulated crystalline fibrillar mesh or scaffold. Examples of such polymers are polyurethane, polyurea, PAN, expanded polytetrafluoroethylene, cellulose triacetate and polyvinylalcohol. The spaces between the fibrils are filed by a continuous phase of hydrophilic polymer with 3-dimensional physical or covalent network (i.e., a hydrogel such as crosslinked polyvinylalcohol or polyvinylpyrrolidone). The most suitable hydrogels for this role are those based on hydrophilic derivatives of polyacrylic and polymethacrylic acid.

The preferred material for the spinal nucleus implant is a synthetic composite of a cellular (or domain) type with continuous phase formed by a hydrophobic polymer or a hydrophilic polymer with low to medium water content forming a "closed cells" spongy structure that provides composite with a strength and shape stability. Examples of suitable polymers are polyurethanes, polyureas, PAN, polydimethylsiloxanes (silicone rubber), and highly crystalline multiblock acrylic and methacrylic copolymers. The polymer has to be sufficiently permeable for water. It is known that even distinctly hydrophobic polymers, such as silicone rubber, can form swellable composites. More preferably, the continuous phase is formed by a strong hydrophilic polymer with sufficient permeability for water but impermeable for high-molecular solutes. Examples of such polymers are highly crystalline hydrogels based on segmented polyurethanes, polyvinylalcohol or multiblock acrylonitrile copolymers with derivatives of acrylic acid. Typically, suitable polymers for the continuous phase in cellular composites have water content in fully hydrated state between about 60% by weight and 90% by weight, preferably between 70 and 85% by weight.

The second component is a highly hydrophilic polymer of high enough molecular weight that cannot permeate through the continuous phase. This component is confined inside the matrix of the continuous phase. The entrapped hydrophilic polymers may be high-molecular weight water-soluble polymers, associative water-soluble polymers or highly swellable hydrogels containing, in fully hydrated state, at least 95% of water and up to 99.8% of water. Such hydrogels are very weak mechanically. However, it does not matter in composites where such polymers' role is generation of osmotic pressure rather than load-bearing, with compression strength in full hydration in the range of 0.01 $MN/m^2$ or lower.

Such system with closed cells (or domains) containing highly swellable or water-soluble polymers can form composites with very high swelling pressure as needed for the spinal nucleus implant function. Examples of suitable hydrophilic polymers are high-molecular weight polyacrylamide, polyacrylic acid, polyvinylpyrrolidone, polyethyleneoxide, copolymers of ethyleneoxide and propyleneoxide or hyaluronic acid; covalently crosslinked hydrogels such as hydrophilic esters or amides of polyacrylic or polymethacrylic acids; and physically crosslinked hydrogels, such as hydrolyzates or aminolyzates of PAN.

Particularly suitable are associative water-soluble polymers capable of forming very highly viscous solutions or even soft physical gels. Preferred are associative polymers containing negatively charged groups, such as carboxylates, sulpho-groups, phosphate groups or sulfate groups. Particularly preferred are associative polymers formed by hydrolysis and/or aminolysis of PAN to high but finite conversions that leave a certain number of nitrile groups (typically, between 5 and 25 molar %) unreacted.

Preferred composites have both continuous phase and dispersed phase formed by different products of hydrolysis or aminolysis of PAN. In this case both components are compatible and their hydrophobic blocks can participate in the same crystalline domains. This improves anchorage of the more hydrophilic component and prevents its extraction. Size of more hydrophilic domains may vary widely, from nanometers to millimeters, preferably from tens of nanometers to microns.

The ratio between the continuous a discrete phase (i.e., between more hydrophobic and more hydrophilic components may vary from about 1:2 to 1:100 on the dry weight basis, but preferred ratio ranges from about 1:5 to 1:20.

Any swellable plastic (e.g. a hydrogel) can be characterized in various ways. The most important characteristic is the liquid content in the state of full hydration. We use the term "Mill hydration" in the usual sense, i.e. meaning equilibrium hydration in full and unrestricted contact with an excess of a liquid of defined composition at a defined temperature, for a time sufficient to achieve equilibrium, without any restriction of sample expansion due to a limited space, availability of swelling liquid or due to an external load or pressure applied against the hydrogel. Unless specifically stated otherwise, the liquid medium is an isotonic unbuffered 0.9% by weight NaCl solution in water, and temperature is the body temperature of 36.5° C.+/−0.5° C.

Dehydrated swellable plastic is often called "xerogel". Another characteristic is compression strength. It can be measured according to ASTM method D695, performed in aqueous immersion. Unless stated otherwise, compressive strength is meant at full hydration and ambient temperature.

Swellable plastics used in the present invention has to have the following basic characteristics:

- Liquid content in the state of full hydration with deionized water at ambient temperature higher than 70% of water and preferably higher than 95% of water.
- Liquid content in the state of full hydration with 0.9% aqueous solution of NaCl at body temperature higher than 65% and preferably higher than 85% of liquid.
- Capability of anisotropical swelling, i.e. capability of a xerogel to expand due to its hydration, even in absence of an external load or any external restriction, in a selected direction or directions more than in other directions. For instance, an anisotropic xerogel rod can increase its diameter while decreasing its length due to its hydration.
- Swellable plastics particularly useful for this invention have modulus of elasticity increasing with deformation. This is important for confinement of radial deformation, i.e. prevention of bulging and herniation under high axial loads. Swellable plastics exhibiting this type of behavior are typically those containing a crystalline phase in their structure.
- Swellable plastics suitable for this invention are those capable of holding "frozen deformation" and to release such deformation in fully hydrated state. Such materials are often called "memory hydrogels" or "memory hydrogel composites". Particularly useful are those materials that are able to hold the "frozen deformation" even in plasticized state at temperatures lower than body temperature. The frozen deformation is released due to hydration, heating to body temperature or a combination of both.

Swellable plastics particularly useful for invention are those with high hydraulic permeability. All hydrophilic plastics, including hydrogels, have relatively high diffusive permeability for water and aqueous solutes. However, the spinal nucleus implant application requires different type of permeability, so called hydraulic permeability, in which the transport is facilitated by pressure gradient rather than concentration gradient. Hydraulic permeability can be characterized by "filtration coefficient" $K_f$. Swellable plastic suitable for the present invention have $K_f > 5.10^{-14}$ [cc.cm-of-thickness/sec.cm$^2$.(dyn/cm$^2$)] and preferably $K_f > 1.10^{-12}$ [cc.cm-of-thickness/sec.cm$^2$. (dyn/cm$^2$)].

The spinal nucleus implant according to the invention have the following characteristics:

The spinal nucleus implant has the fully hydrated volume larger than volume cavity created by a partial or complete removal of nucleus pulposus. The volume of the spinal nucleus implant fully swelled in body fluid at body temperature is preferably by at least 5% larger, and more preferably by at least 10% larger than the volume of the cavity into which the spinal nucleus implant is implanted. The cavity volume is determined at maximum natural separation of vertebra, i.e. with the body in horizontal position.

The spinal nucleus implant according to the invention has three basic shapes:

inherent shape A insertion shape B indwelling shape C

Inherent shape A is corresponding to the most relaxed polymer network in the state of full hydration of the swellable plastic (ie., in -the state with minimum free enthalpy). The spinal nucleus implant in the inherent shape A has cross-section area substantially equivalent to the cross-section area of the cavity vacated by the removal of nucleus pulposus tissue, and height substantial larger than height of such said cavity. (By "height" is meant the dimension substantially parallel with the spinal axis while the "cross-section area" is the area lateral to the spinal axis.) Insertion shape B is the shape of xerogel deformed in such a way that it facilitates insertion and anisotropic swelling in the preferred direction of spinal axis. The xerogel in the shape B and anisotropically dehydrated state has the shape optimized for insertion into the cavity through a small incision in the annulus fibrosus. The preferred shape is an approximate shape of a cylindrical body which length is approximately the length of the longer axis of the nucleus pulposus cross-section. In presence of body fluids and absence of an external load or other spatial restriction. The spinal nucleus implant would spontaneously change from shape B to shape A.

In dwelling shape C is substantially the shape of the cavity created by the partial or complete removal of nucleus pulposus tissue. The spinal nucleus implant is implanted in a partly dehydrated state and in the insertion state A. Once inserted, it imbibes additional water from body fluids and increases its volume until it reaches shape C. The volume in the state C is smaller than in state A and its main dimensions are different. The spinal nucleus implant is partially dehydrated in the shape B because the restriction of space and pressure of surrounding structures does not allow xerogel to reach full hydration. In the shape C, the xerogel has reached substantially the fully hydrated cross-section of the state B. Because of that, it does generate radial swelling pressure that could overly strain the weakened annulus fibrosus and to cause extrusion or herniation. However, the height in the shape C is smaller that the fully hydrated shape A so that the spinal nucleus implant generates swelling pressure preferentially in axial direction.

Once implanted into the cavity in the disc, the spinal nucleus implant according to the present invention swells anisotropically from shape B to shape C, i.e. differently in various directions. For isotropic swelling, which is typical for hydrogels hitherto used in the spinal nucleus implant, relative increase of all linear dimension is the same, and relative increase of any dimension is cubic root of relative volume expansion. For instance, if volume of an isotropic hydrogel increases eight times due to the hydration, any of its linear dimensions (such as thickness, diameter, radius of curvature etc) is doubled.

In the case of anisotropic swelling, the volume change is achieved by preferential expansion in selected directions. More specifically, the spinal nucleus implant according to the present invention swells after implantation more in axial direction than in radial direction (with respect to the spine). It can even swell in the axial direction only, or swell in axial directions while sharing in radial direction. This anisotropic swelling in preferred direction allows generation of swelling pressure in axial direction (that is necessary for vertebral separation) without generating an excessive radial swelling pressure against annulus fibrosus. This feature allows the use of the spinal nucleus implant with fully hydrated volume larger than the cavity volume created by removal of nucleus pulposus tissue. The relative change in the axial direction is higher than the relative change in lateral direction by at least 25% and preferably by at least 100% (i.e., is preferably is twice as large).

Deformed shape B is the shape different from the inherent shape, with its cross-section minimized in order to facilitate its insertion through a small incision. The deformed state is stable as long as the spinal nucleus implant hydrogel is partly or fully dehydrated and as long as temperature is below glass transition temperature and/or melting temperature of at least one polymer phase in the hydrogel The preferred deformed shape B may be that of a flat disc that can be folded for insertion in a taco-style or rolled for insertion into an approximately cylindrical shape ("burrito style"). It can be also folded into a shape of letter M or into other convenient shapes.

The spinal nucleus implant according to the present invention can be made from one or more parts, each of the parts having anisotropic swelling of the spinal nucleus implant described above. Such parts can be individually smaller than the single-piece the spinal nucleus implant, but can be combined into a part that meets the essential the spinal nucleus implant requirements described above. Individual parts can be inserted through-a smaller incision and combined inside the spinal intervertebral disc cavity to perform the spinal nucleus implant function.

For instance, the spinal nucleus implant can be formed by a multitude of individual thin discs, each individually anisotropically swellable (i.e., increasing thickness rather than footprint). These discs are stacked inside the spinal intervertebral disc cavity. Compression during their swelling and the fact that they cannot become fully hydrated will secure sufficient adhesion between layers. The mutual position between layers can be also secured by various means such as sutures, pins, spikes, adhesive layers and so forth The spinal nucleus implant in the shape B can be also formed by a single piece of longitudinal shape (such as a tape) that pushed inside the cavity through a small incision and "assembled" by folding or otherwise stacking to form the desired indwelling shape.

Additional advantage of compound the spinal nucleus implant shapes is improved liquid transport in and out of the device. Insertion through a small incision is facilitated by using a swellable plastic that is sufficiently deformable in the Insertion State. Because many swellable plastics are rigid or even brittle in completely dehydrated state, such plastics can be plastizied by a suitable non-toxic water-miscible liquid such as a salt solution, glycerol, polyethylene glycol, glyceroldiacetate, glycerolformal, dimethylsulfoxide and the like, alone or in combination with water. Another possibility is plastification with a limited about of water, although long-term control of appropriate water concentration can be difficult.

The spinal nucleus implant is implanted into a more o less damaged annulus fibrosus The anisotropic swelling protects the annulus fibrosus against excessive radial swelling pressure that could lead to herniation or extrusion of the spinal nucleus implant material. Additional protection can be provided by an anisotropic deformability of the spinal nucleus implant. Namely, it is desirable that the spinal nucleus implant is more deformable in axial that radial direction. This can be achieved by a multitude of ways. One way is to use a swellable plastic that increases its modulus of elasticity with deformation. This type of behavior is shown by many materials with crystalline component, such as natural rubber, tendon, cartilage, certain type of composites and interpenetrating networks.

This type of behavior can be readily detected from mechanical testing. The benefit can be further improved by radial orientation of the crystalline network in the spinal nucleus implant device made from such swellable plastics.

Another method for limiting radial deformation is in using embedded reinforcement from rigid materials, such as metals, plastics, polymeric fibers etc. Important is proper construction of the reinforcement so that it does not restrict axial deformation. Preferred is helical arrangement, such as embedded metal spring or helically wound fibers. Another possible arrangement is embedded stacked concentric rings. One of suitable reinforcement is knitted structures, e.g. vascular grafts that have similar requirements on anisotropic deformation. Such grafts are made from medically tested materials, which is another advantage. Polymeric reinforcement can be made from medical-grade polyurethanes, polyesters, polyamides and other polymers of sufficient rigidity.

The reinforcement can be advantageously made of permeable hollow fibers, preferably medical-grade hollow fibers used for extracorporeal oxygenators, kidney dialysis or hybrid organs. Such hollow fibers can improve hydraulic liquid transport that is critical for the proper the spinal nucleus implant function.

Metallic reinforcement elements, such as rings or helical springs, can be advantageously used as X-ray markers allowing monitoring of position and deformation status of the implant. They can be used either alone or in a combination with another reinforcement or another X-ray markets.

The spinal nucleus implant is intended as a life-long implant and its high biocompatibility is highly desirable. This can be achieved best by designing the spinal nucleus implant with a continuous highly hydrated surface, preferably with a high content of negatively charged groups, such as carboxylate groups. Particularly preferred is a gradiented surface with carboxylate concentration and hydration increasing from the bulk to the surface. Such surfaces are not only highly biocompatible, but also have very low wet friction as to not erode adjacent tissues, such as the hyaline cartilage of vertebral endplates. Moreover, they will prevent adhesions that could restrict the implant's movement, impede with the liquid transport and complicate the implant removal or replacement if that would become necessary. The preferred method is described in the copending U.S. Pat. No. 5,939,208 (P. Stoy: Method for Creation of Biomimetic Surfaces, issued Aug. 17, 1999).

Preferred manufacturing method comprises the following steps:

(1) Fabrication of the device from suitable swellable plastic. This includes operations such as casting, incorporation of reinforcement, creation of biomimetic surface layer and other operations that may be necessary for fabrication of the selected the spinal nucleus implant design (2) Extraction of impurities in the state of full hydration of the spinal nucleus implant by a suitable aqueous liquid, such as distilled water or an isotonic salt solution. This step may consist of multiple operations, including swelling with an aqueous solution of a plasticizer, such as glycerol.

(3) Dehydration by evaporation of water to a preset degree in a deformed state. Essentially an axial pressure is applied to during the dehydration to impose the deformation. The pressure can be applied throughout the process, or only at the very end of the dehydration process. In that case the essentially dehydrated device is heated, deformed by a pressure using a suitable instrument, and cooled down. This final step is preferably carried out under clean room or even sterile conditions.

(4) Sterilization is carried out after or during the dehydration or deformation process.

The invention and some of the preferred embodiments is further illustrated by the following non-limiting examples.

EXAMPLES:

Example 1

AQUACRYL 90MD hydrogel was purchased from GelMed International s.r.o., V Cibulkach 51, Prague 5, Czech Republic. It is described as acrylic multiblock copolymer with alternating hydrophilic and hydrophobic blocks, hydrophobic block being composed of acrylonitrile units, the hydrophilic blocks from a combination of acrylic acid, acrylamidine and acrylamide units. The molar composition polymer is reported as follows:

| | |
|---|---|
| Acrylonitrile units | 55% |
| Acrylic acid units | 30% |
| Acrylamide units | 9% |
| Acrylamidine units | 6% |

The hydrogel contains 98.6% by weight of liquid at fill hydration by pure water and 90.6% by weight in hydrated in an isotonic NaCl solution (0.9% by weight of NaCl in water).

Tensile strength at ambient temperature and full hydration by isotonic solution is 6 kg per square cm. If fully hydrated by water, the hydrogel is too brittle to measure its tensile or compressive strength (estimated below 1 kg/sq.cm in both cases).

AQUACRYL was supplied as 10% by weight polymer solution in sodium thiocyanate solvent (55% by weight aqueous solution).

Figure 14:
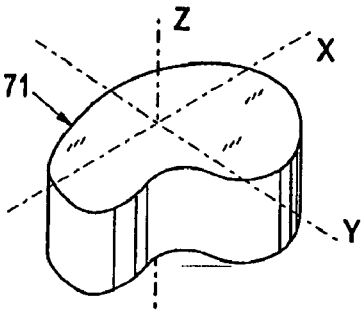
FIGS. 14-18 show alternative embodiments of the present invention.

AQUACRYL was molded in a semi-open porous mold into approximate shape (though not all its dimensions) of nucleus pulposus 71, which is shown in FIG. 14. The footprint or cross-section of nucleus pulposus is kidney-shaped with the largest dimension approximately 40 mm. If we orient this longest dimension in the direction of X-axis in orthogonal coordinates, than the largest dimension in the direction of Y-axis is approximately 20 mm. The height of the space between two vertebra occupied by nucleus pulposus (in the direction of spinal axis and Z-axis of the orthogonal system) is approximately 15 mm. These values are approximate and average. It has to be understood that dimensions of nucleus pulposus differ from disc to disc and from person to person. The height also differs appreciably with time and load applied on the disc.

The porous mold has the cross-section calculated to approximate dimensions of nucleus pulposus cross-section. Calculation was made from known volume fractions of polymer component in the starting solution and the final, fully hydrated hydrogel. The ratio of volumes of the solution to the gel is reciprocal ratio of volume fractions of the polymer in the two systems. Then the ratio of any mold dimension to the corresponding hydrogel dimension is third cube of the ratio of the corresponding volumes. The height of the mold is substantially larger than height of nucleus pulposus.

The AQUACRYL solution was fed into the mold and solidified by coagulation with excess of isotonic saline. Solidified hydrogel was demolded and thoroughly washed with isotonic solution until all sodium thiocyanate is removed.

After the washing the main fully hydrated dimensions in isotonic solution are as follows:

| | |
|---|---|
| Length | 31 mm |
| Width | 18 mm |
| Height | 86 mm |

Figure 15A:
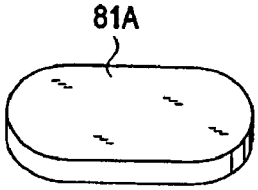
Figure 15B:
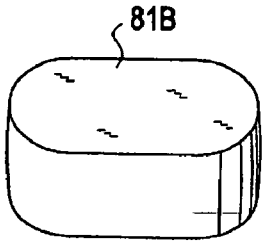

The specimen is cut to 25 mm sections and the dried under axial compression by an increasing load sufficient to maintain the original cross-sectional dimensions. The drying starts at ambient temperature. The drying temperature is gradually increased until reaches 100° C. and xerogel is kept at this temperature for 24 hours. Then it is cooled to ambient temperature. The pressure is maintained until the cooling is completed. Result of this process is a xerogel article of crossection approximately 32×19 mm and thickness approximately 2.5 mm. The device in xerogel state is shown in FIG. 15a as 81 while the same device after reswelling into its inherent, fully hydrated state is shown in FIG. 15b as 81b.

If this xerogel article is immersed into isotonic saline at body temperature, it fully hydrates and swells into original dimensions 31×18×25 mm. The swelling factors in individual axes are as follows: X=0.97; Y=0.95; Z=10.

Part of nucleus pulposus can be surgically removed to create cavity of crossection approximating the implant crossection. This device in its xerogel insertion state is a rigid wafer that can be inserted into the disc via a horizontal slit incision in annulus pulposus. The incision can be secured by suture. Once the implant swells for several hours, in increases it height until it runs against the upper endplate. The continuing swelling increases vertebral separation and stretches annulus pulposus into the shape and tension required for its long-term function. The implant becomes party hydrated and substantially conforms the shape of the cavity created by removal of the tissue. The device in its partly hydrated indwelling state (B) has approximate dimensions of 31×18×15 mm. The swelling factors in individual axes are as follows: X=0.97; Y=0.95; Z=6.

Example 2

AQUACRYL 80MD was acquired from the same source as the hydrogel from Example 1. This grade of AQUACRYL has the same structure and some functional groups, albeit in different proportion:

| | |
|---|---|
| Acrylonitrile units | 79.7% |
| Acrylic acid units | 13.5% |
| Acrylamide units | 4.1% |
| Acrylamidine units | 2.7% |

The hydrogel contains 90.3% by weight of liquid at full hydration by pure water and 79.8% by weight in hydrated in an isotonic NaCl solution (0.9% by weight of NaCl in water). Tensile strength at ambient temperature and full hydration by isotonic solution is 17.3 kg per square cm AQUACRYL 80MD was supplied as 10% by weight polymer solution in sodium thiocyanate solvent (55% by weight aqueous solution).

VISACRYL T2 associative polymer was purchased from GelMed International s.r.o., V Cibulkach 51, Prague 5, Czech Republic. It is described as acrylic multiblock copolymer with alternating hydrophilic and hydrophobic blocks, hydrophobic block being composed of acrylonitrile units, the hydrophilic blocks form a combination of acrylic acid, acrylamidine and acrylamide units. Part of the amide and amidine units is substituted with sulfoethylene groups. The molar composition polymer is reported as follows:

| | |
|---|---|
| Acrylonitrile units | 22.2% |
| Acrylic acid wiits | 51.9% |
| Acrylamide units | 8.5% |
| N-sulfoethylacrylamide units | 6.6 |
| Acrylamidine units | 6.1% |
| N-sulfoethylacrylamidine units | 4.7% |

The polymer is soluble in pure water at an elevated temperature to form shear-thinning, thixotropic solutions at ambient temperature. At ambient temperature polymer does not dissolve but forms soft gels with water concentration 99.5% by weight in pure water and 97.6% by weight in isotonic saline. Polymer was supplied as a granular gel with 5% by weight of solids.

Figure 16A:
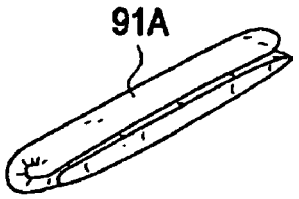
Figure 16B:
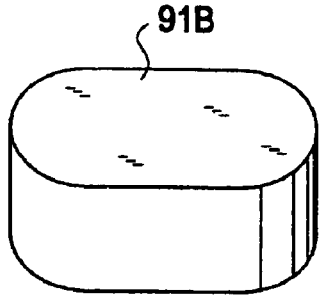

20 weight parts of VISACRYL T2 concentrate was mixed into 80 weight parts of AQUACRYL 80MD solution and mixed in a high-speed blender to form a viscous paste. The mixture was then heated to 60° C. in a closed vessel for 12 hours to remove entrapped air. The paste was filled into the mold from Example 1 and coagulated and washed as described in Example 1. The resulting hydrophilic composite has liquid content over 90% by weight and improved modulus of elasticity and swelling pressure as compared to hydrogel from Example 1. The molded article was soaked for 24 hours in a mixture of 12.5 weight parts of glycerol, 0.9 weight parts of NaCl and 86.6 weight parts of deionized water. It was then cut and dried under stress as described above. After drying, the article was conditioned for 24 hours in air of 60% relative humidity at ambient temperature. The resulting spinal nucleus implants are plasticized and deformable for easier insertion through a small incision. The xerogel implant can be rolled into the insertion shape shown into a cylindrical insertion shape shown as 91a in FIG. 16a. Once inserted into the surgically created cavity, it unfolds and starts its anisotropic expansion into a partially hydrated insertion shape. If it is fully hydrated without mechanical restrictions, it swells into its inherent shape shown as 16b. The implants have similar anisotropic, but faster swelling and higher swelling pressure than product described in Example 1.

Example 3

Hydrogel from the Example 1 was processed in the following way:

The polymer solution was diluted to 7.5% to decrease its viscosity and increase liquid content in the resulting content to 92.3% by weight of isotonic saline.

A strand of twisted polyester fibers was impregnated with the solution, wrapped helically around a lattice made from grass fibers (250 micron diameter) and inserted into the porous mold from Example 1 that was shortened to 25 mm. The mold was then filled with the diluted polymer solution and coagulated with tap water.

After demolding, glass fibers were removed from the gel. The polyester fiber reinforcement was completely embedded in the hydrogel, forming helix coaxial with the device. The reinforcement limited radial deformation of the molding. The channels facilitated drainage of liquid exuded from the hydrogel under axial pressure.

The molding was then washed with isotonic saline and soaked in mixture containing 12.5% of glycerol 0.9% of NaCl and 86.6% of pure water (all % by weight).

Plasticized hydrogel was then dried under pressure as described in Example 1. The result was a flexible wafer of elliptic crossection and thickness 3.5 mm. The wafer can be readily folded or rolled to facilitate implantation as described in Example 2. After implantation, the device swells only axially to achieve vertebral separation by swelling pressure.

Figure 17A:
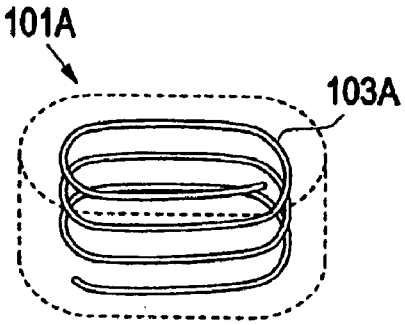
Figure 17B:
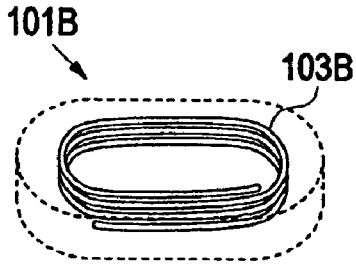

It resists radial expansion under pressure, preventing thus extrusion or herniation in the case that annulus fibrosus is damaged. FIG. 17a shows the implant 101a in its fully hydrated inherent shape, where 103a is the embedded helical fibrous reinforcement in its expanded shape. FIG. 17b shows the implant in its xerogel insertion shape 101b with the fibrous reinforcement 103b in its compressed state.

Example 4

Cylindrical rod of expanded PTFE (GORTEX, Gore Associates), having diameter of 25.2 mm and porosity 45%, was used to swellable form interpenetrating network. The PTFE is axially stretched (up to 3 times) and soaked with a liquid containing 25% glycerol diacetate and 75% of monomer mixture comprising, HEMA (93.4%), EGDMA (0.5%) and methacrylic acid (6%), and dibenzoylperoxide (0.1%). Then axially compressed to 50% of its original length, and the monomers are polymerized under nitrogen at 65° C. The IPN composite can be reshaped for a convenient insertion when heated above 80° C., compressed and cooled under compression.

Swelling of the hydrogel component, outside of the PTFE matrix, in isotonic saline and at body temperature, is 73% by weight. Its compression strength in fully swollen state and outside of PTFE matrix is approximately 0.05 $MN/m^2$. If swollen in isotonic saline, composite expands primarily in axial direction. The swollen IPN composite is more deformable in axial direction than in radial direction. The composite is very strong, resist radial expansion under axial pressure while generating sufficiently high axial swelling pressure. Its components are highly biocompatible and biostable with excellent history in long-term implants. Shape memory allows maintenance of the deformed insertion shape under ambient storage conditions. This combination of properties makes this composite article suitable for use as spinal nucleus implant.

Example 5

Polymer solution from Example 1 is cast as membrane approximately 2 mm thick. The membrane is soaked in a sodium thiocyanate solution to equilibrium and then partly dried to a pre-calculated weight. The conditions were calculated so that the final concentration of sodium thiocyanate in the swelling liquid is 45% by weight.

Figure 18:
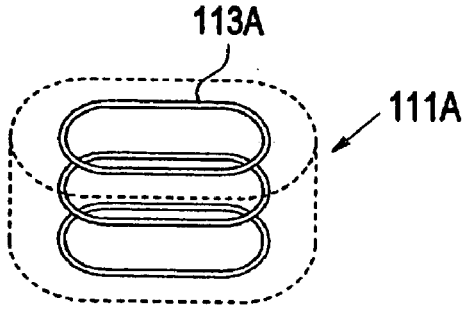

Furthermore, rings of 15 mm diameter are made from nickel-titanium alloy wires with a diameter of 0.75 mm. Foils are now stacked with wire ring placed between each two layers of foil. The stacked assembly is then compressed at 95° C. to cause polymer melting and fusing. After cooling and washing, a block of hydrophilic polymer with embedded ring-shaped reinforcement is formed, as shown in its fully hydrated insertion shape in its fully hydrated insertion shape in FIG. 18 where portion 111a is the hydrated polymer and 113a is the metal reinforcement. The polymer is thoroughly washed in isotonic saline and soaked in diluted glycerol and dried under pressure as described in Example 2.

Figure 2:
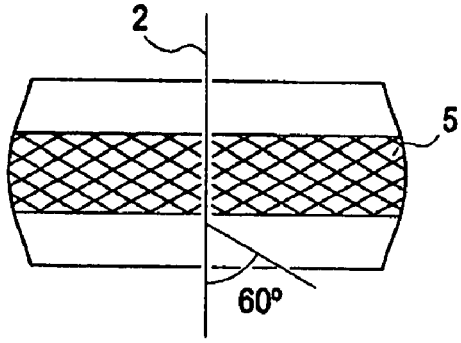

Referring now to FIG. 1, there is shown a spinal intervertebral disc 1 of a living vertebrate such as a human or ape. It includes a nucleus pulposus center 11 and annulus laminates 3, 5, 7 and 9. FIG. 2 shows a flattened partial section of one annulus laminate 5 indicating fibers at a 60° angle to vertical axis 2.

FIGS. 3, 4, 5 and 6 show oblique front views of the spinal intervertebral disc of FIG. 1, in various stages of a surgical procedure of the present invention. Identical parts shown in FIG. 1 are identically numbered in these Figures.

Figure 3:
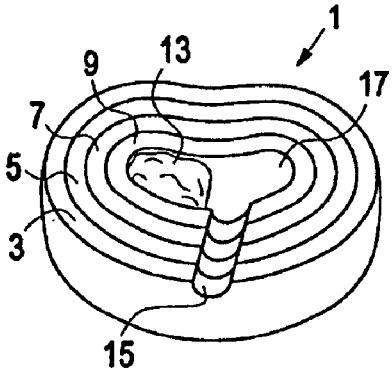
FIGS. 3, 4, 5 and 6 show oblique front views of various steps of a present invention surgical implant procedure, showing cavity creation (nucleus pulposus removal), spinal nucleus implant insertion, unfolded and fully hydrated.

In FIG. 3, an incision 15 has been made and damaged nucleus pulposus has been removed. Remaining nucleus pulposus is shown as area 13, adjacent to cavity 17, the space created from the removal of the damaged nucleus pulposus.

Figure 4:
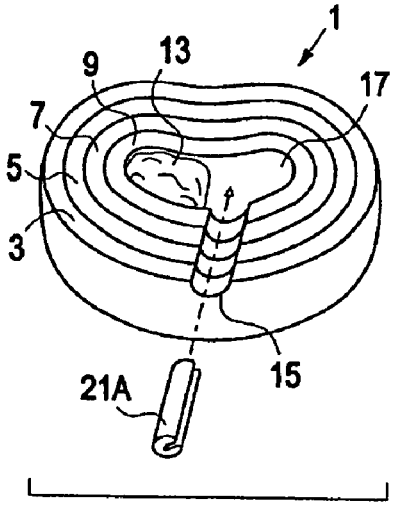
Figure 5:
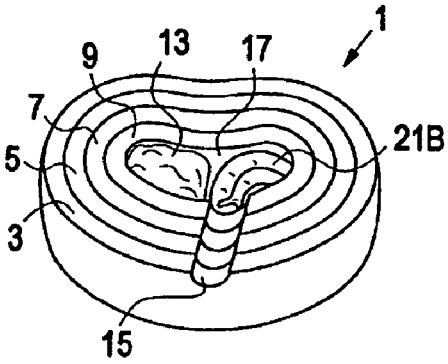
Figure 6:
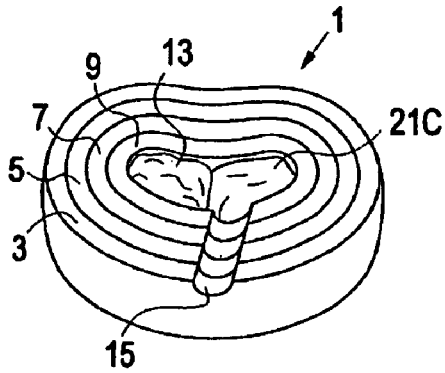
Figure 7A:
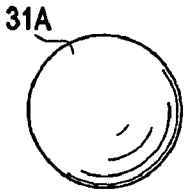
FIGS. 7, 8, 9 and 10 show oblique front views of spherical, cylindrical, helixical and ovate spinal nucleus implant; and, FIGS. 11, 12 and 13 show front cut views of present invention spinal nucleus implant structures.
Figure 7B:
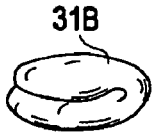
Figure 8A:
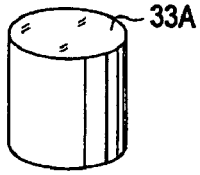
Figure 8B:
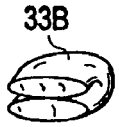
Figure 9A:
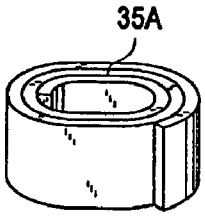
Figure 9B:
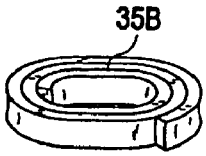
Figure 10A:
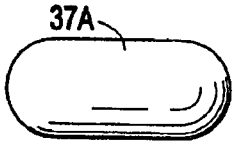
Figure 10B:
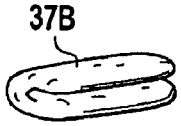

In FIG. 4, present invention spinal nucleus implant 21A is shown in its partially hydrated folded form and is inserted through incision 15 and into cavity 17. FIG. 5 shows spinal nucleus implant 21B (unfolded), located within cavity 17, and FIG. 6 shows spinal nucleus implant 21C and its fully hydrated, enlarged state, subject to volumetric and liquid content changes resulting from osmotic pressure changes, stresses, and movements described above. This spinal nucleus implant is initially formed in accordance with any of the examples set forth above.

Figure 11:
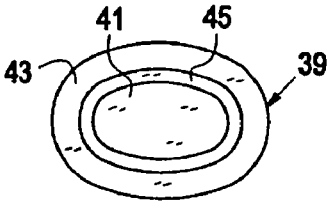

FIGS. 7a, 7b, 8a, 8b, 9a, 9b, 10a and 10b show spinal nucleus implants of the present invention in various forms. The spinal nucleus implants of the present invention in their fully hydrated inherent shapes are shown in the form of sphere 31a, cylinder 33a, helix 35a, and ovoid 37a, respectively. The same implants in their xerogel insertion shapes are shown as biconvex lenticular disc 31b, rolled disc 33b, flattened helix 35b and folded elliptic disc 37b. All forms may include optional embedded reinforcing structures that are not shown in the drawings. FIG. 11 shows a top view of a present invention spinal nucleus implant 39, with a soft, high water content core 41 and an outer jacket with high crystalline polymer content 43. At their interface 45, an optional structural support or transition layer may be included.

Figure 12:
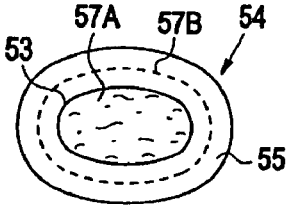

FIG. 12 has a present invention spinal nucleus implant 51 with a core 53 and a jacket 55 and further includes structural support elements 57a in the core and 57b in the jacket.

Figure 13:
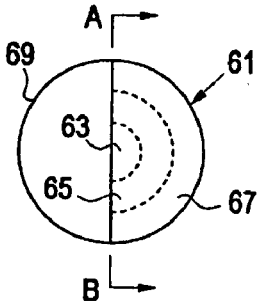

FIG. 13 shows a partially cut present invention spinal nucleus implant sphere 61, cut along line AB. It has a center 63 with a low polymer content and a high water content with a gradient increasing in polymer content and decreasing in water content toward outer layer 69. For example, center 63 may contain ten percent polymer and ninety percent water and layer 65 may contain eighty percent of polymer and twenty percent water and layer 67 may contain thirty percent polymer and seventy percent water and outer surface 69 may contain even more water with a lubricious, negatively charged surface.

Obviously, numerous modifications and variations of the present invention are possible in light of the above teachings. It is therefore understood that within the scope of the appended claims, the invention may be practiced otherwise than as specifically described herein.

What is claimed is:

1. A spinal nucleus implant for replacement of at least a portion of nucleus pulposus tissue removed from a spinal disc of a living vertebrate to restore function of said spinal disc and related vertebral joint, and implantable into the cavity created by said removal of nucleus pulposus tissue, which comprises:

A swellable, biomimetic plastic, having a hydrophobic phase having high crystallinity and low water content and with hydrophilic phase having low crystallinity and high water content, said [biomrimetic] *biomimetic* plastic having an inherent shape in which it has a relaxed polymer network in a state of full hydration, having an insertion shape in which it is at least partially dehydrated to a xerogel state and formable into a compacted mode for maximum efficiency of surgical insertion, and capable of anisotropic expansion due to partial rehydration in situ into an indwelling shape that substantially conforms to the size and shape of said cavity and is capable of osmotic movement of liquid therethrough in response to external pressure change to thereby increase and decrease liquid content in its hydrated state, said anisotropically swellable biomimetic plastic having preferred swelling in a vertical plane and suppressed minimal swelling or swelling in horizontal planes.

2. The spinal nucleus implant of claim 1 wherein said implant is anisotropically deformable in its said indwelling shape having preferred deformability in a vertical plane and suppressed deformability in horizontal planes under compression in the vertical plane.

3. The spinal nucleus implant of claim 1 wherein said swellable, biomimetic plastic is at least partially hydrated in its insertion xerogel state.

4. The spinal nucleus implant of claim 1 wherein said swellable, biomimetic plastic has been formed in a physiologically safe form by being plasticized with a non-toxic liquid in its insertion xerogel state.

5. The spinal nucleus implant of claim 4 wherein said non-toxic liquid is present at a concentration less than 50% by weight of the plasicized [anisotropicafly] *anisotropically* swellable, [biomimnetic] *biomimetic* plastic.

6. The spinal nucleus implant according to claim 3 wherein said non-toxic liquid is selected from the group consisting of glycerol, glycerol monoacetate, glycerol diacetate, glycerylformal, dimethyl sulfoxide, water and mixtures thereof.

7. The spinal nucleus implant according to claim 1 wherein said swellable, biomimetic plastic is a dehydrated anisotropically swellable plastic wherein both said hydrophobic phase and said hydrophilic phase each have hydrophobic and hydrophilic aspects and said hydrophobic phase is a less hydrophilic phase having higher content of hydrophobic groups and said hydrophilic phase is a less hydrophobic phase having higher content of hydrophilic groups, relative to one another.

8. The spinal nucleus implant according to claim 7 wherein said anisotropically swellable, biomimetic plastic comprises non-degradable polymer with a carbon-carbon backbone.

9. The spinal nucleus implant according to claim 7 wherein said less hydrophilic phase is a crystalline phase containing nitric groups.

10. The spinal nucleus implant according to claim 7 wherein said hydrophilic phase has hydrophilic groups which are selected from a group consisting of hydroxyl, carboxyl, carboxylate, amide, N-substituted amide, amidine and N-substituted amidine.

11. The spinal nucleus implant according to claim 1 wherein said swellable, biomimetic plastic has water content more than 70% by weight in said state of [fully] *full* hydration by deionized water.

12. The spinal nucleus implant according to claim 11 wherein said swellable, [biomimnetic] *biomimetic* plastic has water content more than 95% by weight in said state of full hydration.

13. The spinal nucleus implant according to claim 1 wherein said more hydrophilic phase is substantially discrete hydrophilic domains dispersed in a substantially continuous less hydrophilic domain.

14. The spinal nucleus implant according to claim 1 wherein both the hydrophilic phase and the hydrophobic phase are substantially continuous hydrophilic domains and hydrophobic domains forming an interpenetrating network.

15. The spinal nucleus implant according to claim 1 wherein said hydrophobic phase contains crystalline polymer phase detectable by x-ray diffraction.

16. The spinal nucleus implant according to claim 7 wherein said more hydrophobic phase is substantially discrete crystalline domains dispersed in a substantially continuous more hydrophilic domain.

17. The spinal nucleus implant according to claim 1 wherein said swellable, biomimetic plastic has hydrophilic lubricious surface.

18. The spinal nucleus implant according to claim 17 wherein said surface is formed in a gradiented manner with increasing carboxylic groups from the center of said implant towards its outer surface.

19. The spinal nucleus implant according to claim 1 wherein said implantable device has at least the two following structural components:

(a) an inner core from said swellable plastic; and, (b) an outer jacket that is surrounding said core and made from said swellable plastic which is, in its fully hydrated state, less swellable than said inner core.

20. The spinal nucleus implant according to claim 1 including at least one reinforcing element from a substantially non-swellable material embedded in said swellable, biomimetic plastic.

21. The spinal nucleus implant according to claim 19 and further including at least one reinforcing element from a substantially non-swellable material embedded in said swellable, [biomimnetic] *biomimetic* plastic wherein said at least one reinforcing element is located between said jacket and said core.

22. The-spinal nucleus implant according to claim 20 wherein said at least one reinforcing element is made from an implantable material selected from the group consisting of metal, metal alloys, carbon, ceramics, polymer and combinations thereof.

23. The spinal nucleus implant according to claim 22 wherein said polymer is selected from a group consisting of acrylic polymer, methacrylic polymer, polyester, polyurethane, polyurea, polyolefin, halogenated polyolefin, polysaccharide, vinylic polymer, polyphosphazene and polysiloxane.

24. The spinal nucleus implant according to claim 19 wherein said inner core is adherent to and connected to said outer jacket.

25. The spinal nucleus implant according to claim 20 wherein said reinforcing element is more deformable in axial direction than in lateral direction under axial stress.

26. The spinal nucleus implant according to claim 20 wherein said reinforcing element has a general shape selected from the group consisting of helix, ring, elipsoid, cylinder and bellows.

27. A surgical implant procedure for replacing at least a portion of nucleus pulposus tissue removed from a spinal disc of a living vertebrae to restore function of said spinal disc and related vertebral joint, which comprises:

a.) creating a spinal nucleus implant in the form of an anisotropically swellable, biomimetic xerogel plastic, having a two phase structure with a hydrophobic phase having high crystallinity and low water content and with hydrophilic phase having low crystallinity and high water content, said xerogel plastic being capable of anisotropic expansion by rehydration into an inherent shape in which it has a relaxed polymer network in a state of full hydration, and being capable of osmotic movement of liquid therethrough in response to external pressure change to thereby increase and decrease liquid content in its hydrated state said anisotropically swellable biomimetic plastic having preferred swelling in a vertical plane and minimal swelling or suppressed swelling in horizontal planes;

b.) surgically removing at least a portion of nucleus pulposus tissue from a spinal disc of a living vertebrae to create a cavity; and, c.) implanting said spinal nucleus implant into said nucleus pulposus cavity in an at least partially hydrated state.

28. The surgical implant procedure according to claim 27 wherein said spinal nucleus implant, in said fully hydrated state, has volume substantially larger than volume of said cavity vacated by the removal of nucleus pulposus tissue.

29. The surgical implant procedure according to claim 27 wherein said spinal nucleus implant, in said fully hydrated state, has a cross-section area substantially equivalent to the cross-section area of said cavity vacated by the removal of nucleus pulposus tissue, and height substantially larger than the height of said cavity, the "height" being the dimension substantial parallel with the spinal axis and "cross-section area" being the area lateral to the spinal axis.

30. The surgical implant procedure according to claim 27 wherein said xerogel plastic swells in situ substantially more in the direction of the spinal axis than in lateral direction.

31. The surgical implant procedure according to claim 27 wherein said xerogel plastic is implanted in an anisotropically dehydrated state in which its volume is less than 50% of the volume of said cavity vacated by the removal of nucleus pulposus tissue.

32. The surgical implant procedure according to claim 31 wherein said xerogel plastic in its anisotropically dehydrated state has the shape optimized for insertion into the cavity through a small incision in the annulus fibrosus, said shape being an approximate shape of a cylindrical body.

33. The surgical implant procedure according to claim 31 wherein said anisotropically dehydrated state is achieved by anisotropical deformation of said xerogel.

34. The surgical implant procedure according to claim 33 wherein said anisotropical deformation is achieved by heating the xerogel above its glass transition temperature, exposing it to deforming stress in a selected direction, and cooling it down under its glass transition temperature while still exposed to said deforming stress.

35. The surgical implant procedure according to claim 33 wherein said anisotropical deformation is achieved by forming said xerogel by drying the hydrated swellable plastic under a restraining stress, preventing shrinking of xerogel in one or more selected directions.

36. The surgical implant procedure according to claim 35 wherein said restraining stress is an external stress caused by applying pressure in axial direction during the dehydration process.

37. The surgical implant procedure according to claim 35 wherein said restraining stress is created by the presence of internally embedded structure preventing the shrinking in the direction lateral to the axis.

38. The surgical implant procedure according to claim 27 wherein said hydrated implant is under axial stress substantially more deformable in axial direction than in lateral direction.

*39. A spinal disc implant which comprises an implant member dimensioned for positioning in a cavity defined between adjacent vertebrae, the cavity having a first height, the implant member comprising a swellable plastic, whereby upon at least partial hydration of the implant member, the implant member undergoes anisotropic expansion and has a capacity to swell to a second height which is greater than the first height wherein the first height and the second height are measured along a vertical axis and the implant member further defines a horizontal axis and a length extending along the horizontal axis, wherein the capacity to swell to the second height is greater than a swelling capacity along the length of the horizontal axis by at least 25%.*

*40. A spinal disc implant according to claim 39 wherein the cavity defined between the adjacent vertebrae is the disc space.*

*41. A spinal disc implant according to claim 39 wherein the implant further defines a transverse axis to the vertical axis and perpendicular to the horizontal axis, the horizontal axis and transverse axis defining a plane which is transverse to the vertical axis, the implant having a width which is measured along the transverse axis, wherein the implant has a capacity to expand the width along the transverse axis which is at least 25% greater than the expansion of length measured along the horizontal axis.*

*42. A spinal disc implant according to claim 41 wherein the swelling capacity of the implant member defines a cross-section area which is substantially equivalent to the cross-section area of the cavity which has been vacated by removal of nucleus pulposis tissue of a spinal disc.*

*43. A spinal disc implant according to claim 42 further comprising a reinforcing member which assists in limiting the increase in cross-section area of the implant member.*

*44. A spinal disc implant according to claim 43 wherein the reinforcing member is in a form selected from the group consisting of knitted structure, metal spring and helically wound fiber.*

*45. A spinal disc implant according to claim 41 wherein the length of the implant does not expand along the horizontal axis.*

*46. A spinal disc implant according to claim 39 wherein the swellable plastic is a hydrogel.*

*47. A spinal disc implant according to claim 39 wherein the implant member has a water content of more than 70% by weight.*

*48. A spinal disc implant according to claim 39 wherein the implant member is in the form of a xerogel which is dimensioned and configured for insertion through a small incision in an annulus fibrosus.*

*49. A spinal disc implant according to claim 39 wherein the volume of the implant member fully swelled in body fluid at body temperature is at least 5% larger than the volume of the cavity into which the implant is implanted.*

*50. A spinal disc implant according to claim 39 wherein the implant is capable of assuming three configurations:*

(*i*) *an inherent configuration assumed upon full hydration of the implant, the inherent configuration having a cross-section area which is substantially equivalent to the cross-section area of the cavity, wherein the cavity is formed by removal of nucleus pulposis tissue of a spinal disc; and the inherent configuration defining the second height;*

(*ii*) *an insertion configuration assumed upon at least partial dehydration of the implant which has a smaller volume than the inherent configuration, the insertion configuration dimensioned and configured to facilitate insertion through a small incision in an annulus fibrosus; and*

(*iii*) *an indwelling configuration assumed upon insertion of the implant into the cavity vacated by removal of nucleus pulposis tissue of a spinal disc, the indwelling configuration having a cross section area which is substantially equivalent to the cross-section area of the inherent configuration, and a height which is less than the height of the inherent configuration and which is determined by and which corresponds to the height of said cavity whereby positive swelling pressure is generated by the implant between the adjacent vertebrae to increase vertebral separation.*

* * * * *

UNITED STATES PATENT AND TRADEMARK OFFICE

CERTIFICATE OF CORRECTION

PATENT NO. : RE42,837 E
APPLICATION NO. : 10/625390
DATED : October 11, 2011
INVENTOR(S) : Stoy et al.

It is certified that error appears in the above-identified patent and that said Letters Patent is hereby corrected as shown below:

On the Title Page:

Item [64], Replace sub-heading, PCT Filed: with sub-heading, Filed.

Signed and Sealed this
First Day of November, 2011

David J. Kappos

David J. Kappos
*Director of the United States Patent and Trademark Office*